(12) United States Patent
Creighton et al.

(10) Patent No.: US 10,175,184 B2
(45) Date of Patent: Jan. 8, 2019

(54) XRF ANALYZER FOR LIGHT ELEMENT DETECTION

(71) Applicant: Moxtek, Inc., Orem, UT (US)

(72) Inventors: Richard Creighton, Orem, UT (US); Steven Morris, Provo, UT (US); Shawn Chin, Payson, UT (US); Sanjay Kamtekar, Highland, UT (US)

(73) Assignee: Moxtek, Inc., Orem, UT (US)

( * ) Notice: Subject to any disclaimer, the term of this patent is extended or adjusted under 35 U.S.C. 154(b) by 425 days.

(21) Appl. No.: 15/171,803

(22) Filed: Jun. 2, 2016

(65) Prior Publication Data
US 2016/0370307 A1    Dec. 22, 2016

Related U.S. Application Data

(60) Provisional application No. 62/183,082, filed on Jun. 22, 2015.

(51) Int. Cl.
*G01N 23/223* (2006.01)
*H01J 35/24* (2006.01)

(52) U.S. Cl.
CPC ..... *G01N 23/223* (2013.01); *G01N 2223/317* (2013.01); *H01J 35/24* (2013.01)

(58) Field of Classification Search
CPC ...... G01N 23/221; G01N 23/22; G01N 23/20; G01N 1/00; G01N 2223/076; G01N 23/30075; G01N 23/12; G01N 23/223; H01J 35/08; H01J 2235/086; H01J 2235/081
See application file for complete search history.

(56) References Cited

U.S. PATENT DOCUMENTS

| | | | |
|---|---|---|---|
| 6,130,931 A * | 10/2000 | Laurila | G01N 23/223 378/44 |
| 6,882,701 B2 | 4/2005 | Ferrandino et al. | |
| 7,983,386 B2 | 7/2011 | Yellepeddi et al. | |
| 8,064,570 B2 | 11/2011 | Tannian et al. | |
| 2003/0133536 A1 | 7/2003 | Kuwabara et al. | |
| 2008/0181365 A1* | 7/2008 | Matoba | H01J 35/08 378/140 |
| 2008/0192888 A1 | 8/2008 | Iwamoto et al. | |
| 2008/0212739 A1 | 9/2008 | Fukai et al. | |
| 2013/0272497 A1 | 10/2013 | Goto et al. | |
| 2014/0140487 A1 | 5/2014 | Harker et al. | |
| 2014/0219424 A1 | 8/2014 | Smith et al. | |
| 2015/0303024 A1 | 10/2015 | Harker et al. | |

FOREIGN PATENT DOCUMENTS

EP   2672500 A2   12/2013
WO   WO 2014/074742 A1   5/2014

* cited by examiner

*Primary Examiner* — Don Wong
(74) *Attorney, Agent, or Firm* — Thorpe, North & Western, LLP

(57) ABSTRACT

The invention includes an XRF analyzer with reduced x-ray attenuation between sample and target and between sample and detector. Attenuation can be reduced by removing atmospheric-air paths through which the x-rays must travel. Reduced x-ray attenuation can allow for easier detection of low-atomic-number elements. Cost saving can be achieved by reducing the number of x-ray windows.

20 Claims, 3 Drawing Sheets ical-specific, characteristic x-rays. The char- acteristic x-rays can pass through a window in the housing and impinge on the x-ray detector. The x-ray detector can then analyze sample chemistry.

XRF ANALYZER FOR LIGHT ELEMENT DETECTION

CLAIM OF PRIORITY

This application claims priority to U.S. Provisional Patent Application No. 62/183,082, filed on Jun. 22, 2015, which is hereby incorporated herein by reference in its entirety.

FIELD OF THE INVENTION

The present application is related generally to x-ray fluorescence (XRF) analyzers.

BACKGROUND

X-ray fluorescence (XRF) analyzers can include an x-ray source and an x-ray detector. The source can include an electron emitter that is sealed inside of an x-ray tube. The x-ray detector can be sealed inside of an evacuated housing. The electron emitter can emit electrons towards a target that is also within the x-ray tube. The target can then emit x-rays out through a window in the x-ray tube towards a sample. The sample can absorb the x-rays from the source, then fluoresce elemental-specific, characteristic x-rays. The characteristic x-rays can pass through a window in the housing and impinge on the x-ray detector. The x-ray detector can then analyze sample chemistry.

It can be difficult to detect low-atomic-number elements (e.g. $Z \leq 20$ and especially $Z \leq 17$) because of x-ray attenuation by air. This air attenuation occurs between the sample and the window of the x-ray detector and within the detector housing if internal components emitted gasses (out-gassed) after the device has been evacuated and sealed.

Out-gassing can also cause reduced detector cooling (cooling is needed for improved sample analysis resolution). Out-gassing within the x-ray tube can result in gas ion formation due to the electron beam. These gas ions can cause electron spot instability and/or deterioration and early failure of the x-ray tube.

XRF analyzers can be costly due to the high cost of manufacturing two, separate, hermetically-sealed devices— the x-ray tube and the x-ray detector.

SUMMARY

It has been recognized that it would be advantageous to improve detection of low-atomic-number elements, reduce detrimental effects of out-gassing, and reduce manufacturing cost. The present invention is directed to various embodiments of XRF analyzers that satisfy these needs. Each embodiment may satisfy one, some, or all of these needs.

The XRF analyzer can comprise a source and a detector located within an enclosure. The source can include an electron emitter and a target. The electron emitter can emit electrons towards the target and the target can emit x-rays in response to impinging electrons.

In one embodiment, the XRF analyzer can also include an interior of the enclosure that is capable of having a single vacuum therein and a window, for transmission of x-rays, hermetically sealed to the enclosure. The source and the detector can be located within the interior of the enclosure. The target can emit the x-rays towards the window and the detector can face the window and receive and detect x-rays emitted through the window.

In another embodiment, the XRF analyzer can also include a first solid-material-free straight-line path from the detector to the window and a second solid-material-free straight-line path from the target to the window.

In another embodiment, the XRF analyzer can also include a removable or openable cover across an aperture in the enclosure. The detector can face the aperture and can receive and detect x-rays emitted from or through the aperture. A first hermetically-sealed-window-free straight-line path can extend from the detector to the aperture. A second hermetically-sealed-window-free straight-line path can extend from the target to the aperture. The cover can be closeable to protect the source and detector when the XRF analyzer is not in use.

DEFINITIONS

Figure 1:
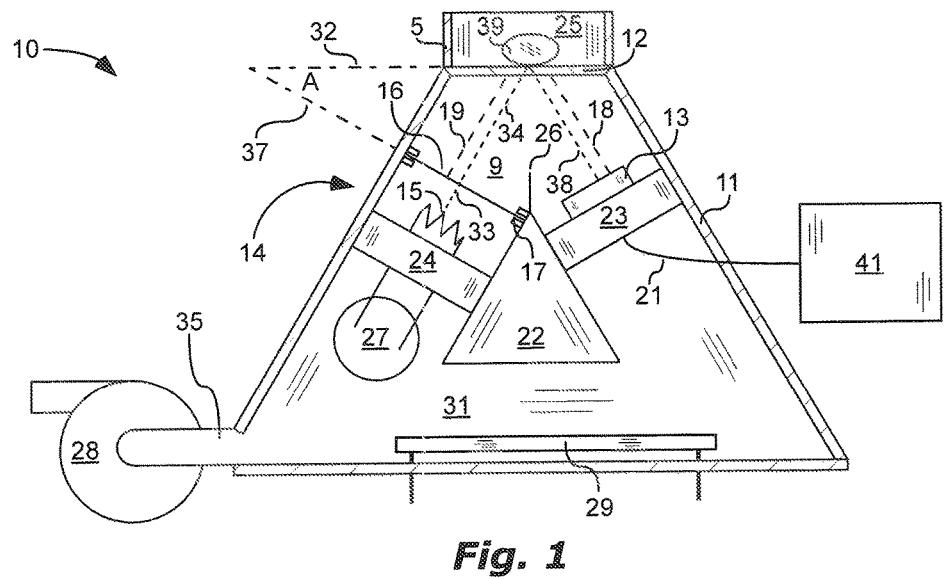
FIG. 1 is a schematic cross-sectional side view of an XRF analyzer 10, showing solid-material-free straight-line paths 18 & 19 from the detector 13 and the target 16 to the window 12, respectively, in accordance with an embodiment of the present invention.

As used herein, the term "detector" means an electronic component for detecting x-rays. Examples of detectors include lithium drifted silicon detector (Si(Li)), silicon drift detector (SDD), and PIN diode. There is no window in front of or attached to the detector except as specified herein.

As used herein, the term "vacuum" means a substantial vacuum, such as is typically found within functional x-ray tubes.

As used herein, the term "single vacuum" in reference to an interior of the enclosure means that there is no hermetically-sealed barrier separating the interior into separate, hermetically-sealed sections. Thus, a single vacuum pump attached to a single port on the enclosure could draw a vacuum throughout the interior of the enclosure.

DETAILED DESCRIPTION

As illustrated in FIGS. 1-5, XRF analyzers 10, 20, 30, and 50 are shown comprising a source 14 and a detector 13 located within an enclosure 11. The XRF analyzers 10, 20, 30, and 50 can be bench-top XRF analyzers. The source can be attached to the enclosure 11. The source 14 can include an electron emitter 15 and a target 16. The electron emitter 15 can emit electrons 33 towards the target 16 and the target 16 can emit x-rays 34 in response to impinging electrons 33. The x-rays 34 can hit and be absorbed by a sample 39. The sample 39 can absorb the x-rays 34 from the source 14, then fluoresce elemental-specific, characteristic x-rays 38. The characteristic x-rays 38 can impinge on the detector 13.

An analyzer 41 can be electrically-coupled to the detector 13. The detector 13, based on the x-rays 38, can send a signal to the analyzer 41. The signal can be sent through wires 21, which can be electrically insulated, or the wires can pass through an electrically-insulative plug in a side of the enclosure 11. The analyzer can receive the signal from the detector 13, and can analyze the signal to determine a material composition of the sample. The analyzer 41 can be located outside of the enclosure 11, as shown, or can be located inside.

The source 14 and the detector 13 can be angled towards where the sample 39 would be located, for more efficient emission and reception of x-rays 34 and 38. There can be a support 22 in or near the center of the enclosure 11 to support the source 14 and the detector 13 and to incline them to face towards the sample 39. The support 22 can be triangle-shaped as shown in the figures. The source 14 and or the detector 13 can attach to and be supported by the support 22 on one side and attach to and be supported by the enclosure 11 on an opposite side.

The electron emitter 15 can attach to the enclosure 11 and support 22 by an electrically-insulative material 24 (e.g. ceramic). Wires of the electron emitter 15 can extend through the enclosure through an electrically-insulative plug 27 in a wall of the enclosure 11 or electrical insulation can be wrapped around each wire. Wires of the electron emitter 15 can be attached to a power supply that can provide appropriate electrical power for the electron emitter 15.

A barrier 26 can be located between the detector 13 and the source 14 and can be positioned to block x-rays 34, emitted from the source 14, from hitting the detector 13. The barrier 26 can attach to and extend from the support 22. The barrier 26 can be metallic. The barrier 26 can comprise tungsten. The barrier can include a high percent of tungsten, such as for example at least 80% tungsten in one aspect, at least 90% tungsten in another aspect, or at least 97% tungsten in another aspect. Tungsten can be a useful barrier 22 material because tungsten has a high atomic number and thus is effective at blocking x-rays and because tungsten is less likely to evaporate and deposit on other XRF analyzer components than some other metals.

The XRF analyzer 10 can be hermetically sealed by a window 12 and can include an interior 31 of the enclosure 11 that is capable of having a single vacuum therein. The source 14 and the detector 13 can be located within the interior 31. The source 14 and the detector 13 can both be windowless, such that there is no individual window for each. The window 12 in the XRF analyzer 10 can be a single window 12. In other words, the window 12 can be the only x-ray window used on the XRF analyzer 10. XRF analyzer 10 can have reduced manufacturing cost because only one hermetically-sealed window 12 is needed (instead of at least two—one on a housing of the detector and one on the x-ray tube).

The electrically-insulative structure 23 and the electrically-insulative material 24 can both have holes or openings along their edges to allow air flow when evacuating or pumping down the interior 31. Thus, there can be an air-flow path, within the interior 31, from the detector 13 to the electron emitter 15, allowing both the detector 13 to the electron emitter 15 to be located in a single vacuum which can be created by a single device.

The XRF analyzer 10 (or other XRF analyzers described herein) can also include a vacuum pump 28 attached to a pump-port 35 in the enclosure 11. The vacuum pump 28 can draw a vacuum within the interior 31 of the enclosure 11. The vacuum pump 28 can operate continuously during XRF analysis. The XRF analyzer 10 can be continually pumped down during use, thus reducing gas molecules with in the interior 31. Thus, there can be reduced gas ions in the interior 31 that can degrade components or cause electron spot movement. There can be fewer gas molecules to attenuate x-rays 34 and 36. A lower vacuum in the interior 31 can also improve detector cooling, and thus improve sample 39 analysis resolution.

Alternatively, the vacuum pump can draw a vacuum throughout the interior 31, then the pump port 35 can be pinched shut. An electrically fired getter 29 can help maintain the vacuum by continual adsorption of gas molecules. A decision of whether to continuously pump or whether to seal off the XRF analyzer 10 can be based on factors such as cost and the benefit of improved vacuum.

The sample 39 can be placed outside of the enclosure 11 and adjacent to the window 12. Thus, x-rays 34 from the target 16 need not pass through air between the x-ray tube 14 and sample as is typical of other XRF analyzers.

Consequently, lower source 14 power is needed due to decreased x-ray 34 attenuation. Also, characteristic x-rays 38 from the sample need only pass through a single window 12, then through a vacuum to the detector 13. Thus, there can be less attenuation of the characteristic x-rays 38 and lower atomic number elements can be more readily detected.

For reduced x-ray 34 & 38 attenuation, there can be an absence of solid material between the detector 13 and the window 12 and between the target 16 and the window 12. In other words, the XRF analyzer 10 can include a first solid-material-free straight-line path 18 from the detector 13 to the window 12 and a second solid-material-free straight-line path 19 from the target 16 to the window 12.

XRF analyzer 10 can also include a cup 25 for holding the sample 39. The cup 25 can be especially useful for liquid and powder samples 39. An annular ring 5 can be sealed to an exterior of the XRF analyzer 10 with the window 12 located at a base of the annular ring 5, thus forming the cup 25. Other XRF analyzers described herein can also include the cup 25.

The cup 25 can be configured to hold a chemical sample 39 for analysis. For example, annular ring 5 and window 12 materials can be suitable (e.g. chemically resistant) for the type of chemical. Also, the cup 25 can be sealed to prevent leakage out of the cup 25.

Figure 2:
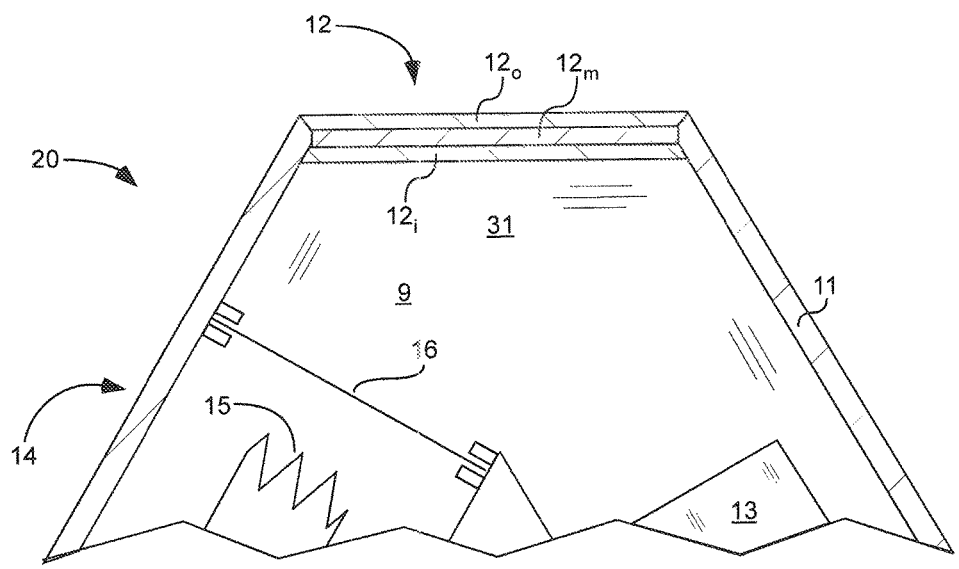
FIG. 2 is a schematic cross-sectional side view of a portion of an XRF analyzer 20, showing an expanded view of the window 12, in accordance with an embodiment of the present invention.

As an example of a corrosion resistant window 12, the window can include a stack of thin film layers. As shown in FIG. 2, the thin film layers can include an outer-layer $12_o$, located farthest from the interior 31, an inner-layer $12_i$, located closest or adjacent to the interior 31, and a middle-layer $12_m$, located between the outer-layer $12_o$ and the inner-layer $12_i$.

In one aspect, the outer-layer $12_o$ can be a corrosion-barrier layer and can be made of or can include amorphous carbon and/or hexamethyldisilazane. The corrosion-barrier layer can be resistant to chemical corrosion from the sample 39. The middle-layer $12_m$ and/or the inner-layer $12_i$ can be an aluminum layer (i.e. made mostly of aluminum). The aluminum layer can provide improved gas impermeability to the window 12.

The middle-layer $12_m$ and/or the inner-layer $12_i$ can be a polymer layer (i.e. made mostly of a polymer). If the polymer layer includes mostly polyimide, then it is called a polyimide layer. The polymer layer can provide structural strength to the window 12. The above described stack of thin film layers is described in more detail in US patent publication number 2014/0140487 and is incorporated herein by reference in its entirety.

It can be important for the window 12 to be sufficiently strong to avoid breakage or excess deflection, to have a high transmissivity of x-rays 34 and 38, to block visible light transmission and/or to block infrared light transmission. For example, the window 12 can have a deflection distance of less than 400 micrometers, a transmissivity of greater than 50% for x-rays 34 and 38 having an energy of 1.74 keV, a transmissivity of less than 10% for visible light at a wavelength of 550 nanometers, and/or a transmissivity of less than 10% for infrared light at a wavelength of 800 nanometers. These window characteristics are described in more detail in U.S. patent application Ser. No. 14/597,955, filed on Jan. 15, 2015, which is incorporated herein by reference in its entirety.

Figure 3:
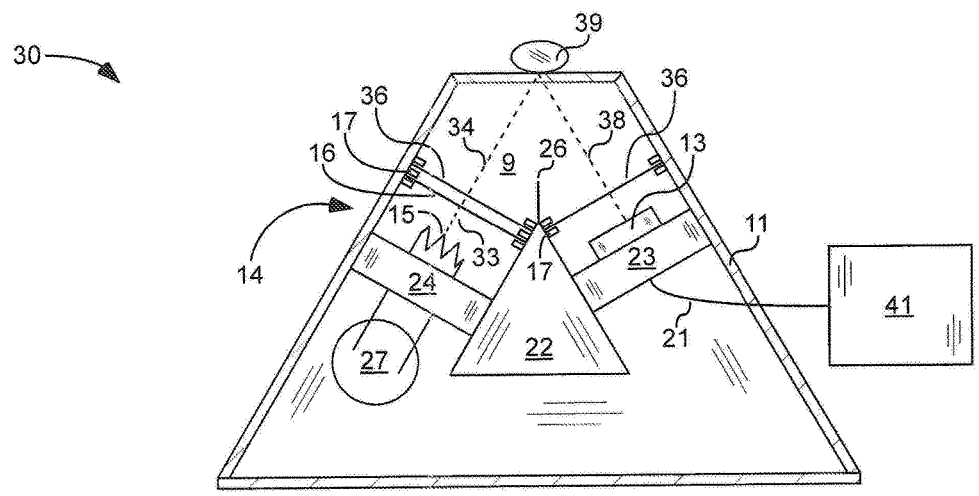
FIG. 3 is a schematic cross-sectional side view of an XRF analyzer 30, showing a removable target 16 and removable filters 36, in accordance with an embodiment of the present invention.
Figure 4:
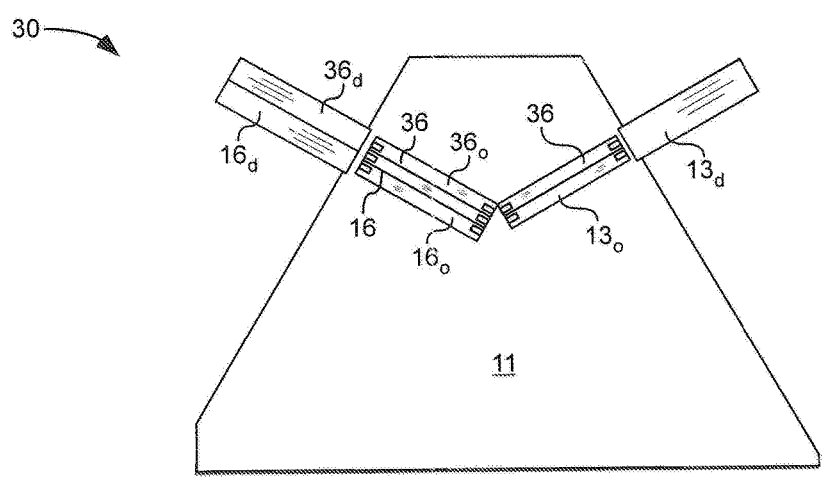
FIG. 4 is a side view of the XRF analyzer 30 of FIG. 3, showing openings $16_o$ and $13_o$ in a wall of the enclosure 11 for replacement of target 16 and filter 36, plus doors $16_d$ and $13_d$ for hermetically sealing the enclosure 11, in accordance with an embodiment of the present invention.

Each XRF analysis can have its own optimal, input x-ray 34 energy spectrum. Thus, it can be important to have the ability to select among different targets 16 for each different XRF analysis. As shown in FIGS. 3 and 4, the target can slide between and be supported by, but not attached to, support members 17. There can be a target-opening $16_o$ in the enclosure 11 that is adjacent or close to the target 16. The target-opening $16_o$ can be sized and located to allow removal and insertion of the target 16, thus allowing the user to select a target 16 that is better suited for each XRF analysis. A target-door $16_d$ can be be openable (i.e. capable of being opened, such as a hinged door for example) or removable for insertion or removal of the target 16 through the target-opening $16_o$. The target-door $16_d$ can allow sealing the XRF analyzer. Thus, the target-door $16_d$ can have a size and material to allow a hermetic seal of the target-door $16_d$ to the enclosure 11 at the target-opening $16_o$.

It can be difficult in an XRF analysis to determine elements in low concentrations. It can also be difficult to distinguish between elements that emit similar energy spectra. Filtration of x-rays 34 emitted from the source 14 or x-rays 38 from the sample 39 can improve analysis in these situations. Filtration of x-rays can provide a narrow energy band specific to a target element, allowing easier detection of that element. A user of an XRF analyzer typically would use the analyzer for detection of multiple, different elements. Thus, the user may desire different filters for different applications.

As shown in FIGS. 3 and 4, the XRF analyzer 30 can include removable filters 36 that are placed between the target 16 and the window 12 and/or between the detector 13 and the window 12. The filters 36 can slide between and be supported by, but not attached to, support members 17, to allow easy removal and insertion.

A source-filter-opening $36_o$ in the enclosure 11 can be sized and located to allow removal and insertion of a filter 36 between the target 16 and the window 12. A source-filter-door $36_d$ can have a size and material for a hermetic seal to the enclosure 11 at the source-filter-opening $36_o$. The source-filter-door $36_d$ can be openable or removable for insertion or removal of the filter 36 through the source-filter-opening $36_o$. The source-filter-opening $36_o$ can be the same opening as, or separate from, the target-opening $16_o$. The source-filter-door $36d$ can be the same door as, or separate from, the target-door $16_d$.

A detector-filter-opening $13_o$ in the enclosure 11 can be sized and located to allow removal and insertion of a filter 36 between the detector 13 and the window 12. A detector-filter-door $13_d$ can have a size and material for a hermetic seal to the enclosure 11 at the detector-filter-opening $13_o$.

The detector-filter-door $13d$ can be openable or removable for insertion or removal of the filter 36 through the detector-filter-opening $13_o$. The detector-filter-opening $13_o$ can be the same as, or separate from, the source-filter-opening $16_o$ and/or the target-opening $16_o$. Thus, there can be one opening for all target and filter insertion and removal or there cal be multiple. The detector-filter-door $13_d$ can be the same as, or separate from, source-filter-door $16_d$ and/or the target-door $16_d$.

The removable filters 36 and/or removable target 16 shown in FIGS. 3-4 can be used in other XRF analyzer designs 10, 20, and 50 described herein.

Figure 5:
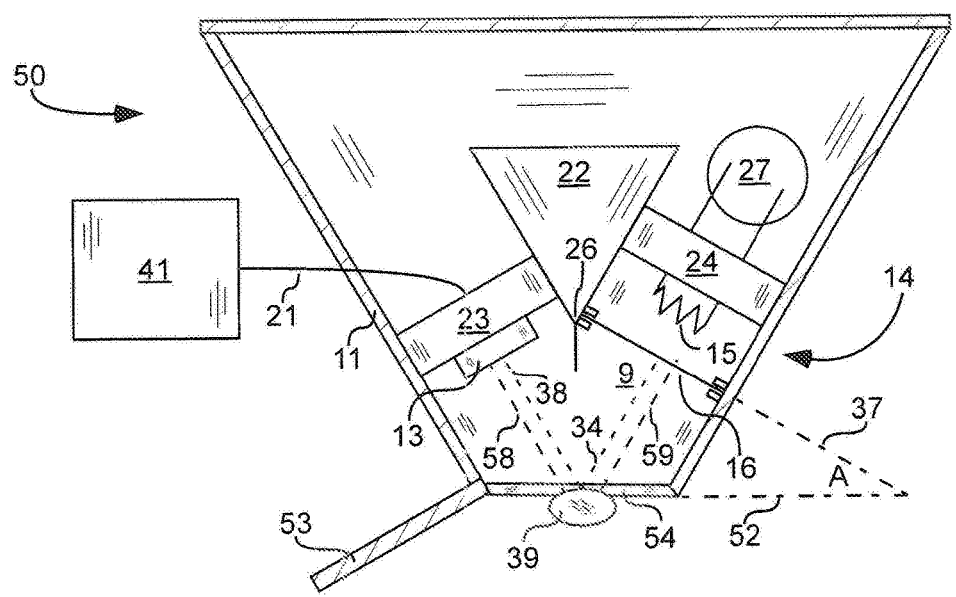
FIG. 5 is a schematic cross-sectional side view of an XRF analyzer 50, with a removable or openable cover 52 across an aperture 54 in the enclosure 11, in accordance with an embodiment of the present invention.

As shown in FIG. 5, the XRF analyzer 50 can include a removable or openable cover 53 across an aperture 54 in the enclosure 11. The XRF analyzer 50 can, with its cover 53 open or removed, be placed in a container and can face a sample 39. The container can then be evacuated for the XRF analysis.

The target can face the aperture 54, typically at an angle A. The target can emit x-rays 34 towards the aperture 54. These x-rays 34 can hit a sample 38. The detector 13 can face the aperture 54, typically at an angle. The detector 13 can receive and detect x-rays 38 emitted from the sample 39. XRF analyzer 50 can be a windowless device, with no x-ray windows.

A first hermetically-sealed-window-free straight-line path 58 can extend from the detector 13 to the aperture 58. A second hermetically-sealed-window-free straight-line path 59 can extend from the target 16 to the aperture 54. The cover 53 can be closeable to protect the source 14 and detector 13 when the XRF analyzer 50 is not in use. The hermetically-sealed-window-free straight-line paths 58 and 59 can be solid-material-free straight-line paths (like paths 18 & 19 in FIG. 1) or can include filters 36, as shown in FIG. 3. XRF analyzer 50 can include removable filters 36 and/or removable target 16 as described above in reference to XRF analyzer 30.

In comparison of XRF analyzer 50 with XRF analyzer 10, XRF analyzer 50 can be advantageous because the XRF analysis can be performed with no window 12 attenuation of x-rays 34 and 38. A disadvantage of XRF analyzer 50 can be a need for an additional container for holding a vacuum during analysis. XRF analyzer 10 might also be more convenient for analysis of liquids.

As shown in FIGS. 1 and 5, acute angle A of target 16 orientation with respect to the window 12 or the aperture 54 can be important for irradiation of the sample 39 and overall size of the XRF analyzer. This orientation is described as follows. A plane aligned with a face of the window 12 defines a window-plane 32 (or aligned with a face of the aperture 54 defines an aperture-plane 52). A plane aligned with a face of the target 16 defines a target-plane 37. An angle A of intersection between the window-plane 32 and the target-plane 37 can be less than 45 degrees in one aspect, less than 30 degrees in another aspect, or less than 20 degrees in another aspect. An angle A of intersection between the aperture-plane 52 and the target-plane 37 can be less than 45 degrees in one aspect, less than 30 degrees in another aspect, or less than 20 degrees in another aspect. Smaller angles allow for smaller overall XRF analyzer size. Cost and separation of voltages are additional factors that may impact selection of angle A for a particular design.

The target 16 can be physically separated from the window 12 (or aperture 54). There can be a solid-material-free gap 9 between the target 16 and the window 12 (or aperture 54). The electron emitter 15, the target 16, and the window 12 (or aperture 54) can be located along a single, straight-line path, with the target 16 between the electron emitter 15 and the window 12 along this straight-line path.

What is claimed is:

1. An x-ray fluorescence (XRF) analyzer comprising:
an enclosure including an interior capable of having a single vacuum therein;
a window, for transmission of x-rays, hermetically sealed to the enclosure;
a source located within the interior of the enclosure, the source including an electron emitter and a target electrically insulated from each other, the electron emitter capable of emitting electrons towards the target and the target capable of emitting x-rays towards the window in response to impinging electrons;
a detector, located within the interior of the enclosure, facing the window and capable of receiving and detecting x-rays emitted through the window;
a barrier located between the detector and the source and positioned to block x-rays, emitted from the source, from hitting the detector, the barrier comprising tungsten; and
an analyzer electrically-coupled to the detector, the analyzer capable of receiving a signal from the detector, the signal based on x-rays impinging on the detector, and analyzing the signal to determine a material composition of a sample.

2. The XRF analyzer of claim 1, wherein the window includes:
a stack of thin film layers including an aluminum layer, a polyimide layer, and a corrosion-barrier layer;
the corrosion-barrier layer comprises a material selected from the list consisting of amorphous carbon or hexamethyldisilazane; and
the corrosion-barrier layer faces an exterior of the enclosure.

3. The XRF analyzer of claim 1, further comprising:
the source and the detector angled towards a sample location;
the source and the detector attached to and supported by a triangle-shaped support on one side and attached to and supported by the enclosure on an opposite side; and
the barrier attached to and extending from the triangle-shaped support.

4. The XRF analyzer of claim 3, wherein:
a plane aligned with a face of the window defines a window-plane;
a plane aligned with a face of the target defines a target-plane; and
an angle of intersection between the window-plane and the target-plane is less than 45 degrees.

5. The XRF analyzer of claim 1, further comprising a first solid-material-free straight-line path from the detector to the window and a second solid-material-free straight-line path from the target to the window.

6. The XRF analyzer of claim 1, further comprising:
a target-opening in the enclosure and a target-door, a source-filter-opening in the enclosure and a source-filter-door, a detector-filter-opening in the enclosure and a detector-filter-door, or combinations thereof;
the target-opening adjacent to the target and located to allow removal and insertion of the target, the source-filter-opening sized and located to allow removal and insertion of a filter between the target and the window, the detector-filter-opening sized and located to allow removal and insertion of a filter between the detector and the window, or combinations thereof; and
the target-door having a size and material for a hermetic seal to the enclosure at the target-opening and being openable or removable for insertion or removal of the target through the target-opening; the source-filter-door having a size and material for a hermetic seal to the enclosure at the source-filter-opening and being openable or removable for insertion or removal of the filter through the source-filter-opening; the detector-filter-door having a size and material for a hermetic seal to the enclosure at the detector-filter-opening, the detector-filter-door being openable or removable for insertion or removal of the filter through the detector-filter-opening; or combinations thereof.

7. An x-ray fluorescence (XRF) analyzer comprising:
an enclosure including an interior capable of having a single vacuum therein;
a window, for transmission of x-rays, hermetically sealed to the enclosure;
a source located within the interior of the enclosure, the source including an electron emitter and a target electrically insulated from each other, the electron emitter capable of emitting electrons towards the target and the target capable of emitting x-rays towards the window in response to impinging electrons;
a detector located within the interior of the enclosure, facing the window and capable of receiving and detecting x-rays emitted through the window;
an analyzer electrically-coupled to the detector, the analyzer capable of receiving a signal from the detector, the signal based on x-rays impinging on the detector, and analyzing the signal to determine a material composition of a sample;
a target-opening in the enclosure and a target-door, a source-filter-opening in the enclosure and a source-filter-door, a detector-filter-opening in the enclosure and a detector-filter-door, or combinations thereof;
the target-opening adjacent to the target, and located to allow removal and insertion of the target, the source-filter-opening sized and located to allow removal and insertion of a filter between the target and the window, the detector-filter-opening sized and located to allow removal and insertion of a filter between the detector and the window, or combinations thereof;
the target-door having a size and material for a hermetic seal to the enclosure at the target-opening and being openable or removable for insertion or removal of the target through the target-opening; the source-filter-door having a size and material for a hermetic seal to the enclosure at the source-filter-opening and being openable or removable for insertion or removal of the filter through the source-filter-opening; the detector-filter-door having a size and material for a hermetic seal to the enclosure at the detector-filter-opening, the detector-filter-door being openable or removable for insertion or removal of the filter through the detector-filter-opening; or combinations thereof.

8. The XRF analyzer of claim 7, further comprising a vacuum pump attached to a pump-port in the enclosure, the vacuum pump capable of drawing a vacuum within the interior of the enclosure.

9. The XRF analyzer of claim 7, further comprising the source and the detector attached to and supported by a triangle-shaped support on one side and attached to and supported by the enclosure on an opposite side.

10. The XRF analyzer of claim 7, further comprising a first solid-material-free straight-line path from the detector to the window and a second solid-material-free straight-line path from the target to the window.

11. The XRF analyzer of claim 7, wherein the XRF analyzer comprises the target-opening and the target-door.

12. The XRF analyzer of claim 7, wherein the XRF analyzer comprises the source-filter-opening and the source-filter-door.

13. The XRF analyzer of claim 7, wherein the XRF analyzer comprises the detector-filter-opening and the detector-filter-door.

14. An x-ray fluorescence (XRF) analyzer comprising:
an enclosure including an interior capable of having a single vacuum therein;
a window, for transmission of x-rays, hermetically sealed to the enclosure;
a source located within the interior of the enclosure, the source including an electron emitter and a target electrically insulated from each other, the electron emitter capable of emitting electrons towards the target and the target capable of emitting x-rays towards the window in response to impinging electrons;
a detector, located within the interior of the enclosure, facing the window and capable of receiving and detecting x-rays emitted through the window;
an analyzer electrically-coupled to the detector, the analyzer capable of receiving a signal from the detector, the signal based on x-rays impinging on the detector, and analyzing the signal to determine a material composition of a sample;
an annular ring sealed to an exterior of the XRF analyzer, forming a cup;
the window located at a base of the annular ring; and
the cup configured to hold a chemical sample for analysis.

15. The XRF analyzer of claim 14, further comprising the source and the detector attached to and supported by a triangle-shaped support on one side and attached to and supported by the enclosure on an opposite side.

16. The XRF analyzer of claim 15, further comprising a barrier located between the detector and the source and positioned to block x-rays, emitted from the source, from hitting the detector, the barrier attached to and extending from the triangle-shaped support.

17. The XRF analyzer of claim 16, wherein the barrier comprises tungsten.

18. The XRF analyzer of claim 14, further comprising a first solid-material-free straight-line path from the detector to the window and a second solid-material-free straight-line path from the target to the window.

19. The XRF analyzer of claim 14, further comprising:
a target-opening in the enclosure and a target-door, a source-filter-opening in the enclosure and a source-filter-door, a detector-filter-opening in the enclosure and a detector-filter-door, or combinations thereof;
the target-opening adjacent to the target and located to allow removal and insertion of the target, the source-filter-opening sized and located to allow removal and insertion of a filter between the target and the window, the detector-filter-opening sized and located to allow removal and insertion of a filter between the detector and the window, or combinations thereof; and
the target-door having a size and material for a hermetic seal to the enclosure at the target-opening and being openable or removable for insertion or removal of the target through the target-opening; the source-filter-door having a size and material for a hermetic seal to the enclosure at the source-filter-opening and being openable or removable for insertion or removal of the filter through the source-filter-opening; the detector-filter-door having a size and material for a hermetic seal to the enclosure at the detector-filter-opening, the detector-filter-door being openable or removable for insertion or removal of the filter through the detector-filter-opening; or combinations thereof.

20. The XRF analyzer of claim 14, wherein the window includes:
a stack of thin film layers including an aluminum layer, a polyimide layer, and a corrosion-barrier layer;
the corrosion-barrier layer comprises a material selected from the list consisting of amorphous carbon or hexamethyldisilazane; and
the corrosion-barrier layer faces an exterior of the enclosure.

* * * * *